(12) United States Patent
Mishra et al.

(10) Patent No.: US 9,568,443 B2
(45) Date of Patent: Feb. 14, 2017

(54) TESTING SYSTEM FOR ESTIMATING THERMAL PROPERTIES OF A MATERIAL

(71) Applicant: Board of Trustees of Michigan State University, East Lansing, MI (US)

(72) Inventors: Dharmendra K. Mishra, East Lansing, MI (US); Kirk D. Dolan, East Lansing, MI (US); James V. Beck, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 642 days.

(21) Appl. No.: 14/054,388

(22) Filed: Oct. 15, 2013

(65) Prior Publication Data

US 2014/0107965 A1 Apr. 17, 2014

Related U.S. Application Data

(60) Provisional application No. 61/713,766, filed on Oct. 15, 2012, provisional application No. 61/844,324, filed on Jul. 9, 2013.

(51) Int. Cl.
*G01N 25/00* (2006.01)
*G01N 25/20* (2006.01)
*G01N 33/02* (2006.01)

(52) U.S. Cl.
CPC .............. *G01N 25/00* (2013.01); *G01N 25/20* (2013.01); *G01N 33/02* (2013.01)

(58) Field of Classification Search
CPC ........ G01N 25/00; G01N 25/20; G01N 33/02; G01K 7/42

(Continued)

(56) References Cited

U.S. PATENT DOCUMENTS 6,111,239 A 8/2000 Park
6,462,316 B1 10/2002 Berkcan et al.
(Continued)

FOREIGN PATENT DOCUMENTS

EP 2063183 A2 5/2009
EP 2098788 A2 9/2009

OTHER PUBLICATIONS

Scheerlinck et al. "Optimal dynamic heat generation profiles for simultaneous estimation of thermal food properties using a hotwire probe: Computation, implementation and validation." Technical Paper, 2008, pp. 297-306, vol. 84, Journal of Food Engineering, 10 pages.

(Continued)

*Primary Examiner* — John H Le
(74) *Attorney, Agent, or Firm* — Howard & Howard Attorneys PLLC (57) ABSTRACT

A testing system for use in measuring thermal properties of material is described herein. The testing system includes a testing apparatus and monitoring system coupled to the testing apparatus. The testing apparatus includes a housing assembly that is configured to receive a material. A heating assembly is coupled to the housing assembly to supply a heat to at least a portion of the material to increase the temperature of the material. A sensing assembly is coupled to the housing assembly and is configured to sense a temperature of the material. The monitoring system comprises a controller having a processor comprising computer-readable instructions for operating the heating assembly to apply a heat to the material volume, receiving signals from the sensing assembly indicative of a temperature of the material, and estimating at least one thermal property of the material utilizing the sensed temperature of the material volume.

16 Claims, 6 Drawing Sheets

(58) Field of Classification Search
USPC .... 702/130, 136; 219/494; 73/25.01; 374/43
See application file for complete search history.

(56) References Cited

U.S. PATENT DOCUMENTS

| | | | |
|---|---|---|---|
| 8,308,350 | B2 | 11/2012 | Yasuda et al. |
| 8,754,351 | B2 | 6/2014 | England et al. |
| 9,074,948 | B2 | 7/2015 | Rankin |
| 9,285,280 | B2 | 3/2016 | Faden |
| 2008/0237215 | A1 | 10/2008 | Lee et al. |
| 2010/0012645 | A1 | 1/2010 | Baier |
| 2013/0048625 | A1* | 2/2013 | Sladecek .................. G01K 7/42 219/494 |

OTHER PUBLICATIONS

Scott et al. "Estimation of Thermal Properties in Carbon/Epoxy Composite Materials during Curing." Technical Paper, 1992, pp. 20-36, vol. 26, No. 1, Journal of Composite Materials, 18 pages.

Shariaty-Niassar et al. "Development of probe for thermal conductivity measurement of food materials under heated and pressurized conditions." Technical Paper, 2000, pp. 133-139, vol. 43, Journal of Food Engineering, 7 pages.

Skrede et al. "Changes in Anthocyanins and Polyphenolics During Juice Processing of Highbush Blueberries (*Vaccinium corymbosum* L.)" Technical Paper, 2000, pp. 357-364, vol. 65, No. 2, Journal of Food Science, 8 pages.

Stasiewicz et al. "Modeling the Effect of Prior Sublethal Thermal History on the Thermal Inactivation Rate of Salmonella in Ground Turkey." Technical Paper, 2008, pp. 279-285, vol. 71, No. 2, Journal of Food Protection, 7 pages.

Sun et al. "Sensitivity analysis and parameter identifiability for colloid transport in geochemically heterogeneous porous media." Technical Paper, Feb. 2001, pp. 209-222, vol. 37, No. 2, Water Resources Research, 14 pages.

Tung et al. "Food properties, heat transfer conditions and sterilization considerations in retort processes." Technical Paper, 1988, pp. 49-71, Food Properties and Computer Aided Engineering of Food Processing Systems, 23 pages.

Ukrainczyk "Thermal diffusivity estimation using numerical inverse solution for 1D heat conduction." Tehcnical Paper, 2009, pp. 5675-5681, vol. 52, International Journal of Heat and Mass Transfer, 7 pages.

Ukrainczyk, et al. "Thermal properties of hydrating calcium aluminate cement pastes." Technical Paper, 2010, pp. 128-136, vol. 40, Cement and Concrete Research, 9 pages.

Van Gelder et al. "A Thermistor Based Method for Measurement of Thermal Conductivity and Thermal Diffusivity of Moist Food Materials at High Temperatures." Technical Paper, 1998, 171 pages, Blackburg, Virginia, 171 pages.

Yajnik et al. "Thermal and Mechanical Effects on Retention of Food-Grade β-carotene during Extrusion Processing." Technical Paper, 2003, 25 pages, vol. 6, Issue 3, Article 10, International Journal of Food Engineering, East Lansing, Michigan, 25 pages.

Yang "A linear inverse model for the temperature-dependent thermal conductivity determination in one-dimensional problems." Technical Paper, 1998, pp. 1-9, vol. 22, Applied Mathematical Modelling, 9 pages.

Yang "Estimation of the temperature-dependent thermal conductivity in inverse heat conduction problem." Technical Paper, 1999, pp. 469-478, vol. 23, Applied Mathematical Modelling, 10 pages.

Yang "Determination of the temperature dependent thermophysical properties from temperature responses measured at medium's boundaries." Technical Paper, 2000, pp. 2161-1270, vol. 43, International Journal of Heat and Mass Transfer, 10 pages.

Yi et al. "Micromachined Hot-Wire Thermal Conductivity Probe for Biomedical Applications." Technical Paper, 2009, pp. 2477-2484, vol. 56, No. 10, IEEE Transactions on Biomedical Engineering, 8 pages.

Zhang et al. "Comparison of HPLC Methods for Determination of Anthocyanins and Anthocyanidins in Bilberry Extracts." Technical Paper, 2004, pp. 688-691, vol. 52, J. Agric. Food Chem, 4 pages.

Zhu et al. "Evaluation of Thermal Properties of Food Materials at High Pressures Using a Dual-Needle Line-Heat-Source Method." Technical Paper, 2007, pp. E49-E56, vol. 72, No. 2, Journal of Food Science, 8 pages.

Zueco et al. "Inverse determination of the specific heat of foods." Technical Paper, 2004, pp. 347-353, vol. 64, Journal of Food Engineering, 7 pages.

Ahmed et al. "Thermal degradation kinetics of anthocyanin and visual colour of plum puree." Technical Paper, 2004, pp. 525-528, vol. 218, Eur Food Res and Technol, 4 pages.

Basu et al. "Prospects for Growth in global Nutraceutical and Functional Food Markets: A Canadian Perspective" Technical Paper, 2007, pp. 637-649, vol. 1(4), Australian Journal of Basic and Applied Sciences, Canada, 13 pages.

Beck "Thermocouple temperature disturbances in low conductivity materials" Technical Paper, 1962 pp. 124-132, Series C, The American Society of Mechanical Engineers (ASME), 10 pages.

Beck "Transient sensitivity coefficients for the thermal contact conductance." Technical Paper, 1967, pp. 1615-1617, vol. 10, Int J Heat and Mass Transfer, Pergamon Press, Great Britain, 3 pages.

Beck "Determination of optimum, transient experiments for thermal contact conductance." Technical Paper, 1969, pp. 621-633, vol. 12, Int J Heat and Mass Transfer, Pergamon Press, Great Britain, 13 pages.

Beck "Nonlinear estimation applied to the nonlinear inverse heat conduction problem." Technical Paper, 1970, pp. 703-16, vol. 13, Int J Heat and Mass Transfer, Pergamon Press, Great Britain, 14 pages.

Beck et al. "Parameter Estimation in Engineering and Science." Book, 1977, pp. 334-417 John Wiley & Sons, 44 pages.

Beck "Sequential Estimation of Thermal Parameters." Journal of Heat Transfer Quarterly Paper, 1977, pp. 314-321, vol. 99, The American Society of Mechanical Engineers (ASME), 9 pages.

Beck et al. "Inverse problems and parameter estimation: integration of measurements and analysis." Introductory Article, 1998, pp. 839-847, vol. 9, Meas Sci Technol, United Kingdom, 10 pages.

Betta et al. "A quick method for thermal diffusivity estimation: Application to several foods." Technical Paper, 2009, pp. 34-41, vol. 91, Journal of Food Engineering, 8 pages.

Bhattacharya et al. "Temperature dependence of thermal conductivity of biological tissues." Technical Paper, Jul. 4, 2003, pp. 769-783, vol. 24, Physiol. Meas., Institute of Physics Publishing, United Kingdom, 16 pages.

Blackwell et al. "Development and implementation of sensitivity coefficient equation for heat conduction problems." Technical Paper, 1999, pp. 15-32, Part B, 36, Numerical Heat Transfer, 18 pages.

Bristow et al. "Measurement of soil thermal properties with a dual-probe heat-pulse technique." Technical Paper, 1994, pp. 1288-1294, vol. 58, Soil Sci Soc Am J, 7 pages.

Bristow et al. "Comparison of Single and Dual Probes for Measuring Soil Thermal Properties with Transient Heating." Technical Paper, 1994, pp. 447-464, vol. 32, Aust. J. Soil Res, 18 pages.

Cemeroglu et al. "Degradation Kinetics of Anthocyanins in Sour Cherry Juice and Concentrate." Technical Paper, 1994, pp. 1216-1218, vol. 59, No. 6, Journal of Food Science, 3 pages.

Chang et al. "Simultaneous Determination of Thermal-Diffusivity and Heat-Transfer Coefficient during Sterilization of Carrot Dices in a Packed-Bed." Technical Paper, 1990, pp. 199-205, vol. 55, No. 1, Journal of Food Science, 7 pages.

Chen et al. "Sensitivity analysis of heat conduction for functionally graded materials." Technical Paper, 2004, pp. 663-672, vol. 25, Materials & Design, 10 pages.

Cui et al. "A new approach for the estimation of temperature-dependent thermal properties by solving transient inverse heat conduction problems." Technical Paper, 2012, pp. 113-119, vol. 58, International Journal of Thermal Sciences 58, 7 pages.

Da Silva et al. "Determination of expressions for the thermal diffusivity of canned foodstuffs by the inverse method and numeri- (56) References Cited

OTHER PUBLICATIONS cal simulations of heat penetration." Technical Paper, 2011, pp. 811-818, vol. 46, International Journal of Food Science and Technology, 8 pages.
De Monte et al. "Diffusion of thermal disturbances in two-dimensional Cartesian transient heat conduction" Technical Paper, 2008, pp. 5931-5941, vol. 51, International Journal of Heat and Mass Transfer, 11 pages.
Denys et al. "Measurement of the thermal conductivity of foods at high pressure." Technical Paper, 1999, pp. 709-713, vol. 64, No. 4, Journal of Food Science, 5 pages.
Dolan "Estimation of kinetic parameters for nonisothermal food processes." Technical Paper, 2003, pp. 728,741, vol. 68, No. 3, Journal of Food Science, 14 pages.
Dolan et al. "Nonlinear regression technique to estimate kinetic parameters and confidence intervals in unsteady-state conduction-heated foods." Technical Paper, 2007, pp. 581-593, vol. 80, Journal of Food Engineering, 13 pages.
Dolan et al. "Parameter estimation for dynamic microbial inactivation; which model, which precision?" Technical Paper, 2013, pp. 401-408, vol. 29, Food Control, 8 pages.
Dowding et al. "Application of sensitivity coefficients for heat conduction problems." Technical Paper, 1998, Thermal Sciences Department 9113, M/S 0835, Sandia National Laboratories, Albuquerque, New Mexico, 13 pages.
Dutta et al. "Rheological characteristics and thermal degradation kinetics of beta-carotene in pumpkin puree." Technical Paper, 2006, pp. 538-546, vol. 76, Journal of Food Engineering, 9 pages.
Giaretto et al. "Two-Wire Solution for Measuremnet of the Thermal Conductivity and Specific Heat Capacity of Liquids: Experimental Design." Technical Paper, May 2004, pp. 679-699, vol. 25, No. 3, International Journal of Thermophysics, 21 pages.
Glatzmaier et al. "Simultaneous measurement of the thermal conductivity and thermal diffusivity of unconsolidated materials by the transient hot wire method." Technical Paper, 1985, pp. 1393-1398, vol. 56 (7), Rev. Sci. Instrum., AIP Publishing, 6 pages.
Gratzek et al. "Solid Food Thermal-Conductivity Determination at High-Temperatures." Technical Paper, 1993, pp. 908-913, vol. 58 No. 4, Journal of Food Science, 6 pages.
Halliday et al. "The thermal conductivity of maize grits and potato granules." Technical Paper, 1995, pp. 273-288, vol. 26, Journal of Food Engineering, Great Britain, 16 pages.
Huang et al. "An inverse problem in simultaneously measuring temperature-dependent thermal conductivity and heat capacity." Technical Paper, 1995, pp. 3433-3441, vol. 38, No. 18, Int. J. Heat Mass Transfer, Great Britain, 9 pages.
Iisakka "Nutraceuticals and functional foods demand for ingredients." Technical Paper, Nov./Dec. 2003, NutraCos, 3 pages.
Koda et al. "Sensitivity analysis of partial differential equations with application to reaction and diffusion processes." Technical Paper, 1979, pp. 259-282, vol. 30, Journal of Computational Physics, 24 pages.
Liang et al. "Microfabricated thermal conductivity sensor: a high resolution tool for quantitative thermal property measurement of biomaterials and solutions." Technical Paper, 2011, pp. 923-928, vol. 13, Biomedical Microdevices, 6 pages.
Manohar et al. "Measurement of Apparent Thermal Conductivity by the Thermal Probe Method." Technical Paper, Sep. 2000, pp. 345-351, Journal of Testing and Evaluation, Pennsylvania, 7 pages.
Mariani et al. "Apparent thermal diffusivity estimation of the banana during drying using inverse method." Technical Paper, 2008, pp. 569-579, vol. 85, Journal of Food Engineering, 11 pages.
Mariani et al. "Estimation of apparent thermal conductivity of carrot purée during freezing using inverse problem." Technical Paper, 2009, pp. 1292-1303, vol. 44, International Journal of Food Science & Technology, 12 pages.
Mishra et al. "Confidence intervals for modeling anthocyanin retention in grape pomace during nonisothermal heating." Technical Paper, 2008, pp. E9-E15, vol. 73, No. 1, Journal of Food Science, 7 pages.
Mishra et al. "Bootstrap confidence intervals for the kinetic parameters of degradation of anthocyanins in grape pomace." Technical Paper, 2011, pp. 1220-1233, vol. 34, Journal of Food Process Engineering, 14 pages.
Mohamed "Simultaneous estimation of thermal conductivity and volumetric heat capacity for solid foods using sequential parameter estimation technique." Technical Paper, 2008, pp. 231-236, vol. 42, Food Research International, 6 pages.
Mohamed "Development of a simple and robust inverse method for determination of thermal diffusivity of solid foods." Technical Paper, 2010, vol. 101, Journal of Food Engineering, 7 pages.
Monteau "Estimation of thermal conductivity of sandwich bread using an inverse method." Technical Paper, 2008, pp. 132-140, vol. 85, Journal of Food Engineering, 9 pages.
Murakami et al. "Recommended design parameters for thermal conductivity probes for nonfrozen food materials." Technical Paper, 1996, pp. 109-123, vol. 27, Journal of Food Engineering, Great Britain, 15 pages.
Murakami et al. "Analysis of Various Design and Operating Parameters of the Thermal Conductivity Probe." Technical Paper, 1996, pp. 209-225, vol. 30, Journal of Food Engineering, Great Britain, 17 pages.
Nahor et al. "Optimal experimental design for the parameter estimation of conduction heated foods." Technical Paper, 2001, pp. 109-119, vol. 48, Journal of Food Engineering, 11 pages.
Oladunjoye et al. "Thermal Diffusivity, Thermal Effusivity and Specific Heat of Soils in Olorunsogo Powerplant, Southwestern Nigeria." Technical Paper, Nov. 2012, pp. 502-521, vol. 13, Issue 2, IJRRAS, 20 pages.
Rao et al. "Engineering Properties of Food." Book, 1986, pp. 223-245, Marcel Dekker, Inc.
Roy "Review of code and solution verification procedures for computational simulation." Technical Paper, 2005, pp. 131-156, vol. 205, Journal of Computational Physics, 26 pages.
Salari et al. "Code Verification by the Method of Manufactured Solutions." Technical Paper, 2000, 124 pages, SAND2000-1444, Sandia National Laboratories, United States, 124 pages.
English language abstract and translation for EP 2063183 extracted from espacenet.com database Jun. 14, 2016, 21 pages.
English language abstract and translation for EP 2098788 extracted from espacenet.com database Jun. 14, 2016, 15 pages.

* cited by examiner

TESTING SYSTEM FOR ESTIMATING THERMAL PROPERTIES OF A MATERIAL

CROSS REFERENCE TO RELATED APPLICATIONS

This application claims priority to and all the benefits of U.S. Provisional Patent Application Ser. No. 61/713,766, filed on Oct. 15, 2012, and U.S. Provisional Patent Application Ser. No. 61/844,324, filed on Jul. 9, 2013, each of the specifications of which is incorporated herein by reference in its entirety.

FIELD OF THE DISCLOSURE

The present disclosure relates generally to testing systems, and more particularly, to testing systems for estimating thermal properties of a material.

BACKGROUND

Functional foods, which have also been referred to as nutraceuticals, are foods that promote health and/or prevent disease. Examples of functional foods include, but are not limited to, omega-3 fatty acids (found in many fish, flaxseed oil, soybean oil, canola oil, and walnuts) which reduce risk of coronary heart disease, blueberries which may have anti-aging effects, and lycopene (found in tomatoes) which has been associated with reduced risk of certain cancers.

Many companies are looking for new ways to develop and incorporate functional foods into their products. Currently, functional foods may be incorporated into a product utilizing high-temperature-short-time (HTST) processes, such as extrusion and aseptic processes. These processes generally require tracking of the food temperature. However, when the food temperature is unknown, the thermal properties of the food may be utilized to estimate the food temperature. The thermal properties of the food may be estimated, for example, using an isothermal line-source method. While this method is useful for determining the thermal properties of the food at low temperatures (e.g. temperatures less than 100° C.), this method often poses a challenge when estimating thermal properties at high temperatures (e.g. temperatures greater than 100° C.). This is due, at least in part, to the degradation of the quality of the food as the food is exposed to the high temperatures. In many instances, the nutrients in the food are degraded and the food ends up burned or even charred.

Accordingly, there is a need for a convenient and efficient testing system for estimating the thermal properties of a material (such as food) at temperatures greater than 100° C.

SUMMARY

A testing system for use in measuring thermal properties of material comprises a testing apparatus, and monitoring system coupled to the testing apparatus. The testing apparatus comprises a housing assembly having a sidewall with a first end, a second end, and an inner surface that defines a cavity extending between the first and second ends along a longitudinal axis. The housing assembly is configured to receive a material. A fluid supply system is coupled to the housing. The fluid supply system is configured to supply a pressurized fluid into the cavity to pressurize the housing. A heating assembly is coupled to the housing assembly. The heating assembly comprises at least one heating element that is positioned within the housing cavity. The heating element extends along the longitudinal axis and at least partially through the material. The heating assembly is configured to supply a heat to at least a portion of the material to facilitate increasing a temperature of the material. A sensing assembly is coupled to the housing assembly. The sensing assembly includes at least one sensing element that is positioned within the housing cavity. The sensing element is positioned within the material and is configured to sense a temperature of the material. The monitoring system includes a controller that is coupled to the heating assembly and the sensing assembly. The controller comprises a processor comprising computer-readable instructions for operating the heating assembly to apply a heat to the material, receiving from the sensing assembly signals indicative of a temperature of the material, and estimating at least one thermal property of the material utilizing the sensed temperature of the material.

The testing system of the present disclosure may be used to estimate the thermal properties (e.g. thermal conductivity and specific heat) of a material at a temperature above 100° C. The testing system is equipped with a testing apparatus and a monitoring system for sensing a temperature change at various locations within the material. The thermal properties of the material are estimated based on the temperature changes at each measured location. In an example, the thermal properties of the material are estimated, by a controller of the monitoring system, using a non-isothermal, inverse line-source method. Furthermore, estimation of the thermal properties of the material is accomplished during a single (i.e., one) experiment.

Additionally, the thermal properties of the material can be estimated utilizing the testing system in a manner of minutes (e.g. less than 3 minutes and, in some instances, less than 2 minutes). This is compared to other currently available systems, which typically require numerous isothermal experiments and long wait periods for the sample to equilibrate to the next experimental temperature. In many instances, the quality of the food is degraded even before reaching the temperatures that are greater than 100° C. The testing system is also configured to simultaneously measure the temperature changes within the material at a plurality of locations, which significantly reduces the cost of determining the thermal properties of the material.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

The testing system described herein may be used to estimate the thermal properties of a material (e.g. food) in a single experiment at a temperature above 100° C. The testing system may also be used to estimate the thermal properties of a material in a single experiment across a temperature range of 20° C. to 140° C.

The testing system is designed to simultaneously sense a temperature change in the material at a plurality of sensing locations. For instance, the testing system includes a testing apparatus designed to heat the material via conduction heating, and a monitoring system designed to measure temperature changes at a plurality of sensing locations within the material. In an example, the monitoring system is designed to simultaneously measure the temperature changes at the plurality of sensing locations within the material. The thermal properties of the material are estimated based, at least in part, on the sensed temperature changes within the material.

An example of the testing system 10 will be described at least with reference to FIGS. 1-7. The testing system 10 includes a testing apparatus 12 configured to contain a material, supply a heat to the material to facilitate increasing a temperature of the material, and sense a change in temperature in the material at a plurality of sensing locations within the material. In an example, the material is an organic material such as food. It is to be understood that the testing system 10 be configured to estimate the thermal properties of any material including organic materials and/or inorganic materials.

The testing apparatus 10 generally includes a housing assembly 16, a fluid supply system 18, a heating assembly 20, and a sensing assembly 22.

Figure 1:
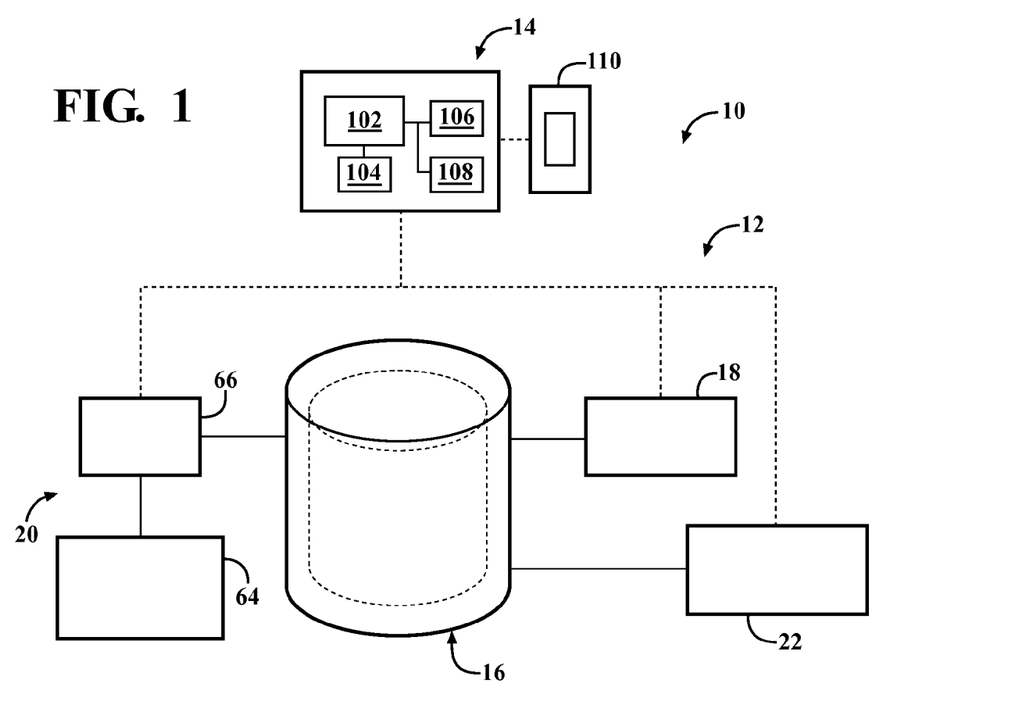
FIG. 1 schematically depicts an example of a testing system.
Figure 2:
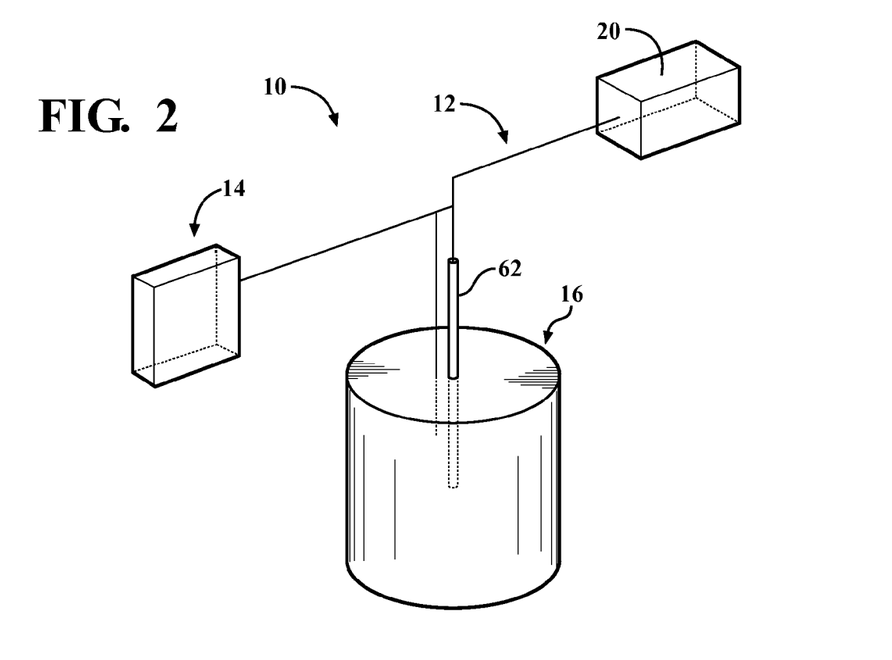
FIG. 2 schematically depicts another example of the testing system.
Figure 3:
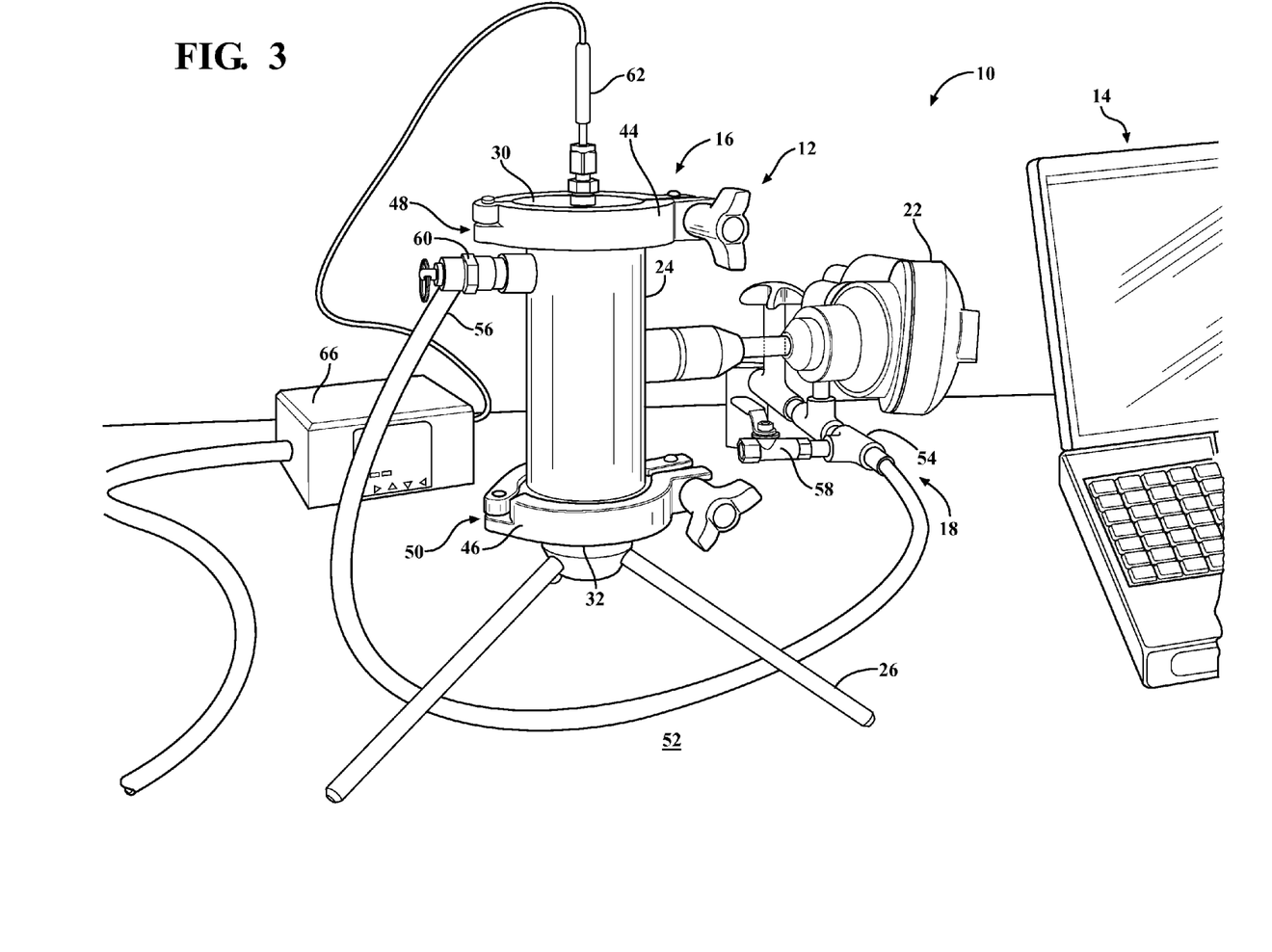
FIG. 3 is a perspective view of another example of the testing system.

As shown in FIGS. 3-6, the housing assembly 16 includes a housing 24 and a support assembly 26. The housing 24 includes a sidewall 28 having a first end 30, a second end 32, and an inner surface 34 that defines a cavity 36. In one example, the inner surface 34 has a substantially cylindrical shape. In another example, the inner surface 34 has any suitable shape that enables the testing system 10 to function as described herein. Further, the cavity 36 extends between the first 30 and second 32 ends along a longitudinal axis A. The cavity 36 is configured to receive a volume of material 40, such as an organic material. As best shown in FIG. 3, the housing assembly 16 further includes a first end cap 44 coupled to the first end 30, and a second end cap 46 coupled to the second end 32 of the housing 24. In one example, the housing 24 is formed from a stainless steel. In another example, the housing 24 is formed from a metal alloy, aluminum, a plastic, and/or any suitable material that enables the testing system 10 to function as described herein.

Still with reference to FIG. 3, the housing assembly 16 also includes a first clamping assembly 48 designed to couple the first end cap 44 to the first end 30 of the housing 24. In addition, the housing assembly 16 includes a second clamping assembly 50 designed to couple the second end cap 46 to the second end 32 of the housing 24.

Additionally, the support assembly 26 is coupled to the second end 32 of the housing 24 for supporting the housing 24 on a supporting surface 52, such as a table top or the like.

The fluid supply assembly 18 is coupled to the housing 24 for channeling a pressurized fluid into the cavity 36. The pressurized fluid may be, for example, air, water, gas, and/or any suitable pressurized fluid. The fluid supply assembly 18 further includes a pressurized fluid source 54 and a supply line 56 disposed between the housing assembly 16 and the fluid source 54 for channeling the pressurized fluid from the fluid source 54 to the housing assembly 16. A fluid control valve 58 is disposed between the fluid source 54 and the supply line 56 for adjusting a flow of the pressurized fluid from the fluid source 54 to the housing assembly 16. A pressure relief valve 60 is coupled to the sidewall 28 of the housing 24 for regulating an internal pressure of the cavity 36. The pressure relief valve 60 is also configured to selectively enable fluid to be channeled from the cavity 36 to the environment outside of the housing, which reduces an internal pressure within the cavity 36. This will maintain the internal pressure of the cavity 36 at a predefined pressure.

Figure 4:
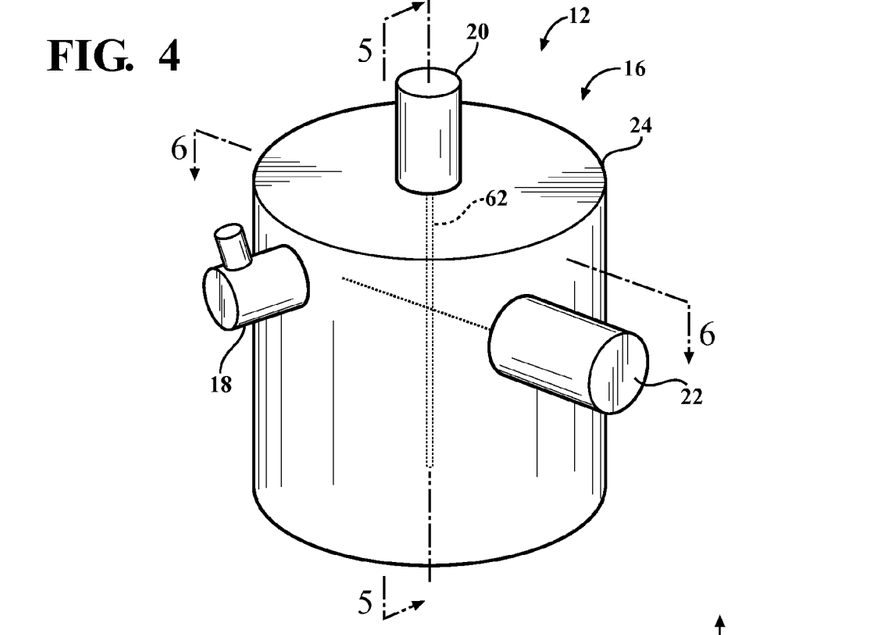
FIG. 4 is an enlarged, perspective view of an example of a testing apparatus for the testing system.

The heating assembly 20 is coupled to the housing assembly 16 and is designed to supply a heat to at least a portion of the material 40, which will increase a temperature of the material 40. In an example, the heating assembly 20 includes at least one heating element 62 (such as a heating probe) that is positioned within the cavity 36 (as shown in FIG. 4, for instance). A power supply assembly 64 is coupled to the heating element 62, and a temperature controller 66 is coupled to the power supply assembly 64 and to the sensing assembly 22. The heating assembly 20 is generally configured to heat the material 40 via conduction. In an example, the heating assembly 20 is configured to heat the material 40 to a temperature of from about 0° C. to about 140° C. In another example, the heating assembly 20 is configured to heat the material 40 to a temperature of from about 20° C. to about 130° C. In still another example, the heating assembly 20 is configured to heat the material 40 to a temperature above 130° C.

In an example, the testing system 10 includes at least one thermocouple (not shown) to measure a temperature rise at a particular location within the material 40. In another example, the testing system 10 does not have a thermocouple, and the controller 100 relies on the resistance of the heating element 62 to determine the temperature rise at the particular location within the material 40. Details of the controller 100 are set forth below. It is to be understood that the testing system 10 may physically have a thermocouple, but does not have to use the thermocouple to measure the temperature rise. Said differently, despite the presence of a thermocouple, the testing system 10 may rely on the resistance of the heating element 62 alone to determine the temperature rise.

In an example, a stainless steel cup may be used as the housing 24 to hold the material 40 and the heating element 62. The housing 24 is pressurized to allow expected maximum temperature of about 140° C. Pressure fittings may also be used to accommodate the heating element 62 and thermocouples. Furthermore, pressurized air may be connected from a pressurized tank to the housing 24 with a three-way valve, and a safety valve may be installed on the housing 24 to limit the maximum pressure rise. While the safety valve can be set to a maximum pressure rating of 50 psi, the pressure rating of the housing 24 can be greater than 100 psi.

The power supply assembly 64 is coupled to the heating element 62 to provide a power to the heating element 62 so that the heating element 62 can supply a heat to the material 40 inside the cavity 36. The power supply assembly 64 is also configured to selectively adjust a power voltage supplied to the heating element 62 so that the amount of heat supplied to the material 40 can be adjusted.

The temperature controller 66 is configured to sense a temperature of the material 40 and/or of the sidewall 28 of the housing 24. The temperature controller 66 is also configured to control the power supply assembly 64 to adjust the heat supplied to the material 40 based at least in part on the sensed temperature of the material 40 and/or the sensed temperature of the sidewall 28 of the housing 24.

Figure 5:
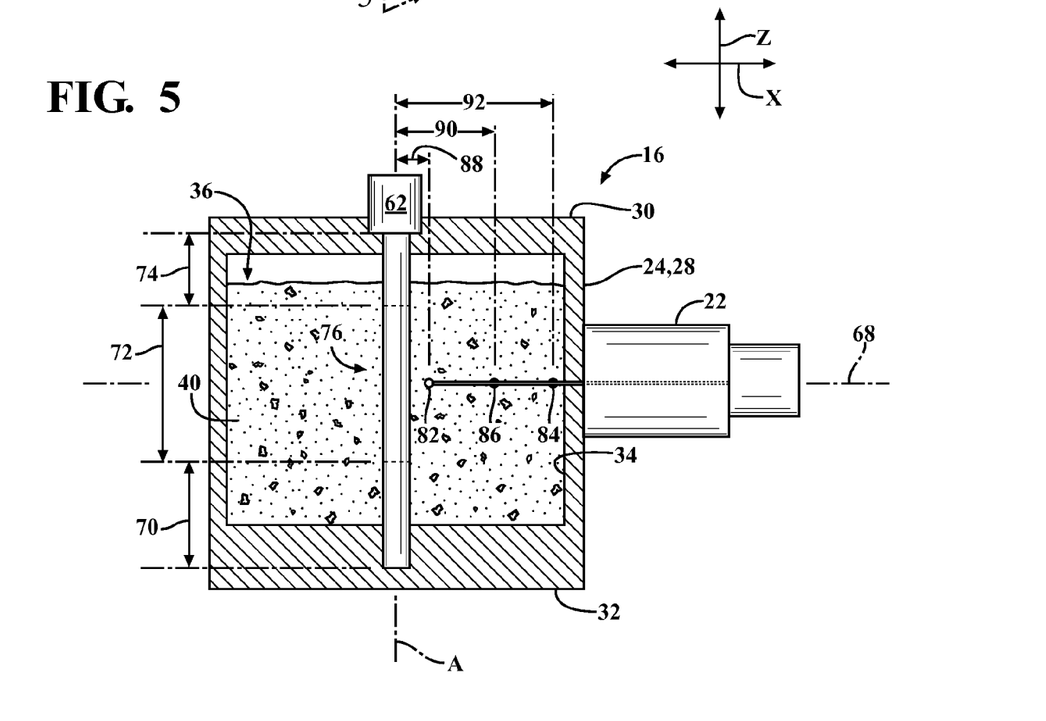
FIG. 5 is a partial cross-sectional view of the testing apparatus shown in FIG. 4 taken along line 5-5.
Figure 6:
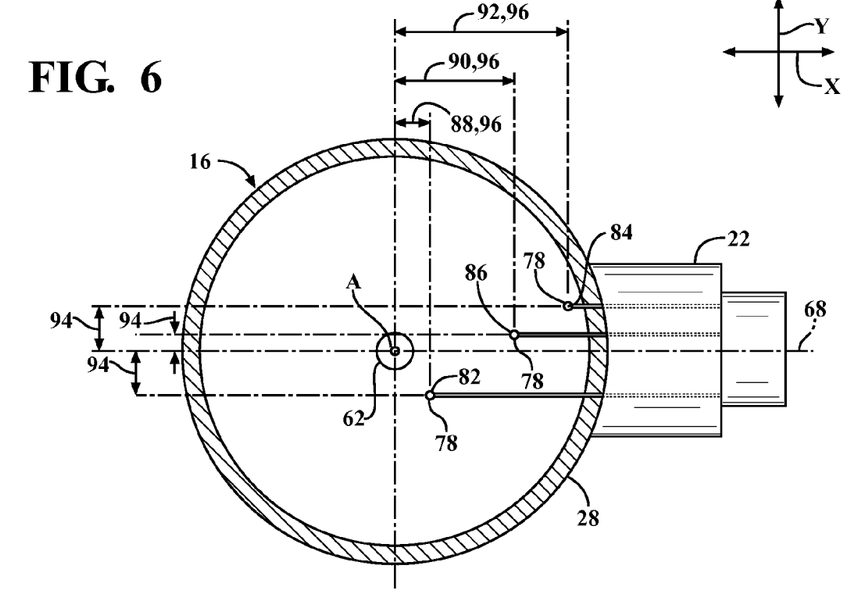
FIG. 6 is another partial cross-sectional view of the testing apparatus shown in FIG. 4 taken along line 6-6.

As best shown in FIGS. 4-6, three perpendicular axes X, Y, and Z are used to define a three-dimensional Cartesian coordinate system relative to the housing assembly 16. Specifically, the Z-axis is orientated to extend substantially coaxially through the longitudinal axis A of the housing assembly 16. The X-axis and the Y-axis intersect to form a reference plane 68 within housing assembly 16. In one example, the heating element 62 is coupled to the first end cap 44 and extends through the first end cap 44 such that the heating element 62 is positioned within the cavity 36. The heating element 62 is also orientated along the longitudinal axis A, and extends at least partially through the material 40. In the illustrated example, the heating element 62 includes a first portion 70, a second portion 72, and a third portion 74. The third portion 74 is coupled to the first end cap 44 and extends outwardly from the first end cap 44 towards the second end cap 46. The second portion 72 is defined between the third portion 74 and the first portion 70. The first portion 70 extends outwardly from the second portion 72 towards the second end cap 46.

In the illustrated example, the heating element 62 is configured to radiate heat from the second portion 72 to define a heating region 76 along the heating element 62. The second portion 72 of the heating element 62 supplies heat to the material 40 inside the cavity 36. In addition, the heating element 62 does not radiate heat from the first portion 70 and the third portion 74. In an alternative example, the heating element 62 is configured to radiate heat from the first portion 70, the second portion 72, and/or the third portion 74, and to transfer heat to the material 40 at any location along the heating element 62.

As shown in FIGS. 5 and 6, the sensing assembly 22 is coupled to the housing 24, and a portion of the sensing assembly 22 extends into the cavity 36. In an example, a portion of the sensing assembly 22 also extends into the material 40. The sensing assembly 22 is configured to sense a temperature of the material 40 at a plurality of sensing locations 78 within the material 40. More specifically, in the illustrated example, the sensing assembly 22 is orientated with respect to the heating element 62 such that the sensing assembly 22 senses a temperature of the material 40 at a plurality of sensing locations 78 that extend radially outwardly from the heating element 62. In this example, each sensing location 78 is spaced radially outwardly from an adjacent sensing location 78. In one example, the sensing assembly 22 is orientated substantially perpendicularly with respect to the heating element 62 so that each sensing location 78 is orientated within the same reference plane 68. Additionally, and in another example, the sensing assembly 22 is orientated with respect to the second portion 72 so that the temperature of the material 40 is sensed within the heating region 76.

The sensing assembly 22 includes a plurality of sensing elements 82, 84, 86 that are positioned within the material 40, and the sensing elements 80 define each sensing location 78. In an example, the sensing assembly 22 includes an inner sensing element 82, an outer sensing element 84, and a middle sensing element 86. The inner sensing element 82 is positioned nearest to the heating element 62, while the outer sensing element 84 is positioned farthest from the heating element 62. The middle sensing element 86 is positioned between the inner sensing element 82 and the outer sensing element 84, where the inner sensing element 82 is positioned nearer to the heating element 62 than the middle sensing element 86 and the outer sensing element 84 is positioned nearer to the housing inner surface 34 than the middle sensing element 86. Additionally, the inner sensing element 82 is positioned a first radial distance 88 from the heating assembly 20, the middle sensing element 86 is positioned a second radial distance 90 from the heating assembly 20 and is greater than the first radial distance 88, and the outer sensing element 84 is positioned a third radial distance 92 that is greater than the second radial distance 90. In one example, each radial distance 88, 90, and 92 are approximately equal. Alternatively, each radial distance 88, 90, and 92 may be different.

In addition, and in the example depicted in FIG. 6, each sensing element 82, 84, and 86 may be spaced an axial distance 94 from the X-axis within the reference plane 68. In this example, each axial distance 94 is different. Additionally, each sensing element 82, 84, and 86, may be spaced an axial distance 96 from the Y-axis within the reference plane 68.

Figure 7:
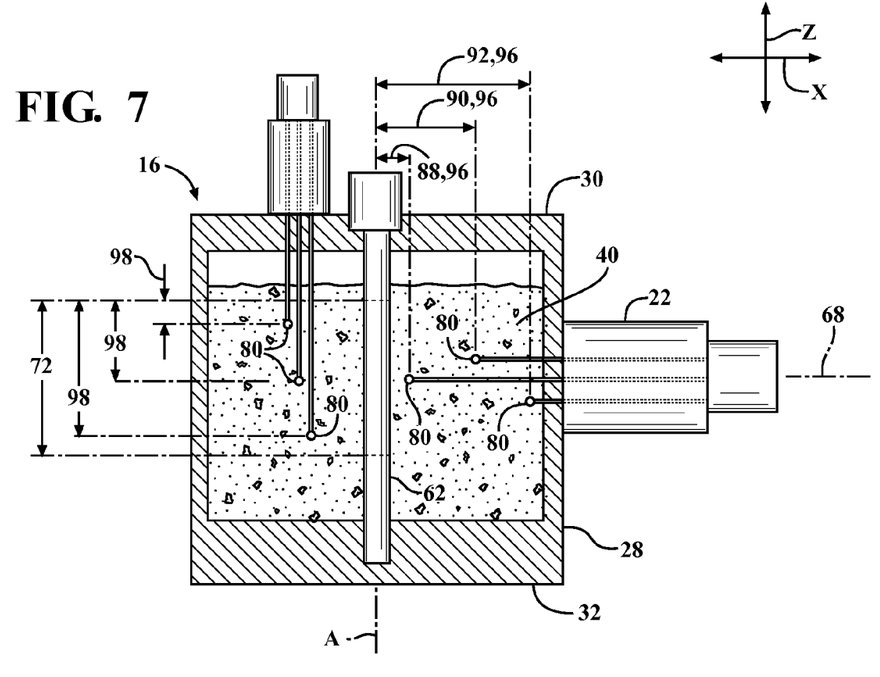
FIG. 7 is partial cross-sectional view of another example of the testing apparatus.

Referring now to FIG. 7, in another example, the sensing assembly 22 includes a plurality of sensing elements (all of which are identified by reference numeral 80) that are spaced a distance 98 from the reference plane 68 along the Z-axis. These sensing elements 80 are designed to sense a temperature of the material 40 within plurality of reference planes. In addition, and in an example, the testing apparatus may include a plurality of sensing assemblies 22. A portion of the plurality of sensing assemblies 22 extend within the material 40, and are designed to sense a temperature within the material 40 at a plurality of sensing locations along the Z-axis and at various radial distances from the heating element 62.

As previously mentioned, the testing system 10 further includes a monitoring system 14 coupled to the testing apparatus 12. The monitoring system 14 is configured to estimate thermal properties of the material 40 based on the temperature changes at each measured location within the material 40.

Referring again to FIGS. 1-3, the monitoring system 14 includes a controller 100 coupled to the heating assembly 20 and the sensing assembly 22. In one example, controller 100 includes a processor 102 that is in communication with a memory device 104 for executing programmed instructions. In some examples, executable instructions are stored in memory device 104. Alternatively, executable instructions may be retrieved from another device via a computer network. The controller 100 is programmable to perform one or more operations described herein by programming the processor 102. For instance, the processor 102 may be programmed by encoding an operation as one or more executable instructions and providing the executable instructions in the memory device 104. The processor 102 may include, but is not limited to, a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. It is to be understood that methods of estimating the thermal properties described hereinbelow may be encoded as executable instructions embodied in a non-transitory computer readable medium, including, without limitation, a storage device and/or a memory device. Such instructions, when executed by a processor, cause the processor to perform at least a portion of the methods described herein. It is further to be understood that the above examples are merely illustrative, and are not intended to limit in any way the definition and/or meaning of the term processor.

In an example, the memory device 104 is one or more devices that enable information, such as executable instructions and/or other data, to be selectively stored and retrieved. The memory device 104 may include one or more computer readable media, such as, without limitation, dynamic random access memory (DRAM), static random access memory (SRAM), a solid state disk, and/or a hard disk. The memory device 104 may be configured to store, without limitation, executable instructions and/or any other type of data suitable for use with the methods described herein.

The controller 100 further includes a presentation interface 106 coupled to the processor 102. The presentation interface 106 is configured to output (e.g., display, print, and/or otherwise output) information (such as a plurality of traces corresponding to a sensed temperature over a predefined period of time) to a user (not shown). For example, the presentation interface 106 may include a display adapter 110 that is coupled to a display device, such as a cathode ray tube (CRT), a liquid crystal display (LCD), an organic LED (OLED) display, and/or an "electronic ink" display. In some examples, the presentation interface 106 includes more than one display device.

The controller 100 includes an input interface 108 that receives input from the user. The input interface 108 is coupled to the processor 102 and may include, for example, a keyboard, a pointing device, a mouse, a stylus, a touch sensitive panel (e.g., a touch pad or a touch screen), a gyroscope, an accelerometer, a position detector, a toggle switch, a selector dial, and/or an audio input interface. A single component, such as a touch screen, may function as both a display device of the presentation interface 106 and as the input interface 108.

The controller 100 is configured to operate the heating assembly 20 to selectively apply a heat to the material 40. The controller 100 receives signals that are indicative of a temperature of the material 40 at the plurality of sensing locations 78 from the sensing assembly 22, and determines at least one thermal property of the material 40 based, at least in part, on the sensed temperature of the material 40.

During testing, the monitoring system 14 is configured to increase a heat supplied to the material over a predefined period of time, sense a temperature increase within the material over the predefined period of time, calculate a rate of change in temperature of the material within the predefined period of time, display a trace indicative of the calculated change in temperature for each sensed location on presentation interface 106, and determine at least one thermal property of the material 40 based, at least in part, on the calculated temperature change.

In addition, the monitoring system 14 is configured to reduce the heat applied to the material 40 upon sensing the material temperature is approximately equal to a predefined temperature, sensing a temperature of the material at each sensing location over a second predefined period of time, calculate a rate of change in temperature at each sensing location during the second period of time, and determine at least one thermal property of the material based, at least in part, on the calculated rate of temperature change at each sensing location during the second period of time.

The examples described herein may be performed using a computer-based and/or computing-device-based operating environment as described above. A computer or controller may include one or more processors or processing units, system memory, and some form of non-transitory computer-readable media. Example non-transitory computer-readable media include flash memory drives, hard disk drives, digital versatile discs (DVDs), compact discs (CDs), floppy disks, and tape cassettes. By way of example and not limitation, computer-readable media comprise computer storage media and communication media. Computer-readable storage media are non-transitory and store information such as computer-readable instructions, data structures, program modules, or other data. Communication media typically embody computer-readable instructions, data structures, program modules, or other data in a modulated data signal such as a carrier wave or other transport mechanism and include any information delivery media. Combinations of any of the above are also included within the scope of computer-readable media.

Although described in connection with an example computing system environment, the examples of the testing system are operational with numerous other general purpose or special purpose computing system environments or configurations. Examples of well known computing systems, environments, and/or configurations that may be suitable for use with aspects of the invention include, but are not limited to, mobile controllers, personal computers, server computers, hand-held or laptop devices, multiprocessor systems, gaming consoles, microprocessor-based systems, set top boxes, programmable consumer electronics, mobile telephones, network PCs, minicomputers, mainframe computers, distributed computing environments that include any of the above systems or devices, and the like.

Also disclosed herein is a method of estimating the thermal properties of the material 40. In one example, heat is applied to the material 40 to facilitate increasing a temperature of the material 40. The heat is applied at a heating location positioned within the material 40. A temperature of the material 40 is sensed at a plurality of sensing locations 78, where adjacent sensing locations 78 are spaced radially outwardly from the heating location within the material 40. At least one thermal property of the material 40 is estimated based at least in part on the sensed temperature at each sensing location 78.

As previously mentioned, thermal properties of the material 40 are estimated, by the controller 100, using a non-isothermal inverse line-source estimation method. Generally, isothermal line-source methods utilize sufficiently small temperature changes (e.g. a 0.5 to 2° C. temperature rise) so that the thermal properties have negligible change(s) over that temperature range. In "non-isothermal line-source methods", on the other hand, thermal properties of the material 40 change significantly with temperature during rapid heating. It is believed that during rapid heating, degradation of the material 40 does not occur, because the material 40 does not have time to degrade.

In an example, the testing system 10 includes at least one thermocouple for measuring the temperature of the material 40. Utilizing the temperature measurements, the thermal properties (such as heat capacity (C(T)) and specific heat (k(T))) of the material 40 may then be estimated utilizing Equation (1):

$$\frac{1}{r}\frac{\partial}{\partial r}\left(k(T)r\frac{\partial T}{\partial r}\right) = C(T)\frac{\partial T}{\partial t} \quad \text{Equ. (1)}$$

where T is temperature (° C.), r is the radial direction (m), and t is time (s). Typically, the initial temperature of the material 40 is uniform and is represented by Equation (2):

$$T(r,0) = T_i \qquad \text{Equ. (2)}$$

In Equation (1) above, k(T) and C(T) are input as linear functions of temperature. Further, the spatial domain (i.e., the size of the housing 24) is sufficiently large so that the outer boundaries do not affect the temperature distribution near the heating element 62. Further, the heating element 62, which in this example is represented by a heating probe, can also be approximated by a thermally lumped body with volumetric energy generation (g) in W/m$^3$. The boundary condition at the radius of the heating element 62, which is represented by R, is shown by Equation (3):

$$-k\frac{\partial T}{\partial r}(R,t) = g\frac{R}{2} - C_{probe}\frac{R}{2}\frac{\partial T}{\partial t}(R,t) \qquad \text{Equ. (3)}$$

The amount of time needed to estimate the thermal properties of the material in a single experiment may be determined as follows. Assuming that the housing 24 is infinite, the temperature will not change along the Z-axis. It is also assumed that the housing 24 has a radius of 2 cm, the heating element 62 has a length of 4 cm, and a thermocouple junction is present about half-way along the length of the heating element 62 (i.e., x=2 cm). To ensure that the temperature at the junction will be affected less than 1% by the tip of the heating element 62, a dimensionless number $\alpha t/(x)^2$ should be less than 0.05 with a being approximately equal to $2\times10^{-7}$ m$^2$/s. Solving for t gives a value of about 100 s. Doing a related calculation to minimize the effect of the sidewall 28 of the housing 24 on the temperature measurement gives t of about 400 s. The shorter time (which is about 100 s) is the maximum amount of time needed in a single experiment to estimate the thermal properties of the material 40.

The amount of power that the heating element 62 needs may be determined as follows. The geometry of the heating element 62 is treated as a thermally lumped body with uniform energy generation inside the body. In an example, the radius of the heating element 62 is about 0.00033 m, and the radius of the housing 24 is about 0.02 m. For a 100 s temperature duration, the Fourier number based on the radius R of the heating probe is $\alpha t/R^2$, which is 183 in this example. For many food products of intermediate moisture, k is about 0.5 W/m° C. Accordingly, for a constant flux solution when $\alpha t/R^2$ is 183, a dimensionless temperature $(T(r,t)-T_i)/(q_0 R)/k$ is determined to be about 3.01. Since it is desirable to have a temperature rise of about 100° C. (e.g. 25° C. up to 125° C.), the equation immediately above may be used to estimate $q_0$ to be about 50,337 W/m$^2$. The surface area of the heating probe is also equal to $\pi DL$, and the amount of power of the heating probe is determined by multiplying $q_0$ by the surface area of the heating probe. In this example, about 4.2 W of power is needed to ensure there is a 100° C. temperature rise within 100 s.

It is to be understood that scaled sensitivity coefficients may be used to improve the thermal property estimation. The sensitivity coefficient of a property is, for instance, the first partial derivative of a function involving the property. For the function T=f(k,C,x,t), the sensitivity coefficients of k and C are $$\frac{\partial T}{\partial k} \text{ and } \frac{\partial T}{\partial C},$$

respectively. After multiplying the scaled sensitivity with the property or parameter, scaled sensitivity coefficients represented by $$X'_k = k\frac{\partial T}{\partial k} \text{ and } X'_C = C\frac{\partial T}{\partial C}$$

for k and C, respectively, can be obtained.

Typically, the sum of the scaled sensitivity coefficients is not equal to zero when estimating the thermal properties. Accordingly, a linear dependence cannot be present. For instance, if the measured quantity is temperature T, the linear dependence relationship is shown in Equation (4):

$$A_1\beta_1\frac{\partial T}{\partial\beta_1} + A_2\beta_2\frac{\partial T}{\partial\beta_2} + \ldots + A_p\beta_p\frac{\partial T}{\partial\beta_p} = 0 \qquad \text{(Equ. 4)}$$

where at least one of the coefficients $A_i$ is not zero and the $i^{th}$ scaled sensitivity coefficient is defined to be a scaled sensitivity coefficient for parameter $$\beta_i = X'_{\beta_i} = \beta_i\frac{\partial T}{\partial\beta_i}.$$

For consistent units, each $A_i$ coefficient is equal to unity. A linear relationship can then occur, and the thermal properties can be simultaneously estimated.

It is further to be understood that numerical codes are useful for providing a solution to partial differential equations, and verification of these codes is equally as useful. An intrinsic verification method (IVM) to the numerical solution of the partial differential equation is presented below. Derivation of the dimensionless form of scaled sensitivity coefficients is also presented below. It is to be understood that the sum of scaled sensitivity coefficients is used in the dimensionless form to provide a method for verification.

IVM is based on the scaled sensitivity coefficients and can be used in the verification of the numerical codes, as well as to perform thermal property estimation.

The transient heat conduction equation in a hollow container for temperature-variable thermal conductivity and volumetric heat capacity (caused by changes in the specific heat) can be given by Equations (5) and (6) below:

$$\frac{1}{r}\frac{\partial}{\partial r}\left(k_1 f_k(T,K)r\frac{\partial T}{\partial r}\right) + \frac{\partial}{\partial z}\left[k_1 f_k(T,K)\frac{\partial T}{\partial z}\right] = C_1 f_C(T,C)\frac{\partial T}{\partial t} \qquad \text{Equ. (5)}$$

$$R_1 < r < R_2, 0 < z < Z, t > 0$$

where $$K = \frac{k_2}{k_1}, C = \frac{C_2}{C_1} \qquad \text{Equ. (6)}$$

Linear functions of temperature for the thermal conductivity and volumetric heat capacity are also considered, which are shown by Equations (7) and (8):

$$f_k(T, K) = 1 + \frac{T - T_1}{T_2 - T_1}(K - 1) \quad \text{Equ. (7)}$$

$$f_C(T, C) = 1 + \frac{T - T_1}{T_2 - T_1}(C - 1) \quad \text{Equ. (8)}$$

These equations give the thermal conductivity value of $k_1$ at $T_1$ and $k_2$ at $T_2$. Further, the temperature dependence causes Equation (7) to be linear in T. The boundary conditions are shown by Equations (9) and (10):

$$-k_1 f_k(T, K) \frac{\partial T}{\partial x}(R_1, z, t) = q_0 f(t) \quad \text{Equ. (9)}$$

$$\frac{\partial T}{\partial r}(R_2, z, t) = 0 \quad \frac{\partial T}{\partial z}(r, 0, t) = 0 \quad \frac{\partial T}{\partial z}(r, Z, t) = 0 \quad \text{Equ. (10)}$$

where the function on the right of Equation (9) is known, as well as the $q_0$. Further, the initial condition is given by Equation (11):

$$T(r, z, 0) = T_1 \quad \text{Equ. (11)}$$

The above problem is put into a dimensionless form, as shown by Equation (12):

$$\tilde{r} \equiv \frac{r}{R_1}, \quad \text{Equ. (12)}$$

$$\tilde{R}_2 \equiv \frac{R_2}{R_1},$$

$$\tilde{z} \equiv \frac{z}{R_1} \quad \tilde{t} \equiv \frac{k_1 t}{C_1 R_1^2},$$

$$\tilde{T} \equiv \frac{T - T_1}{\frac{q_0 R_1}{k_1}},$$

$$\theta_2 \equiv \frac{T_2 - T_1}{\frac{q_0 R_1}{k_1}}$$

Further, the partial derivatives of temperature T are found, as shown by Equation (13):

$$T - T_1 = \quad \text{Equ. (13)}$$

$$\frac{q_0 L}{k_1} \tilde{T}\big(\tilde{x}, \tilde{R}_2, \tilde{z}, \tilde{t}(k_1, C_1), K(k_1, k_2) C(C_1, C_2), \theta_2(k_1, T_2 - T_1)\big)$$

The derivative of equation (13) with respect to $k_1$, $k_2$, $C_1$, $C_2$ and $T_2 - T_1$ are found and are added together to get Equation (14):

$$k_1 \frac{\partial T}{\partial k_1}\bigg|_{k_2, C_1, C_2, T_2 - T_1} + \quad \text{Equ. (14)}$$

$$k_2 \frac{\partial T}{\partial k_2}\bigg|_{k_1, C_1, C_2, T_2 - T_1} + C_1 \frac{\partial T}{\partial C_1}\bigg|_{k_1, k_2, C_2, T_2 - T_1} +$$

$$C_2 \frac{\partial T}{\partial C_2}\bigg|_{k_1, k_2, C_1, T_2 - T_1} + (T(x, t, k_1, k_2, C_1, C_2) - T_1) -$$

$$(T_2 - T_1) \frac{\partial (T - T_1)}{\partial (T_2 - T_1)}\bigg|_{x, t, k_1, k_2, C_1, C_2} = 0$$

The sensitivity coefficients are for fixed x and t values, and the final derivative is the rate of change in the computed temperature when the specified temperature $T_2$ is changed. Equation (14) indicates that the properties $k_1$, $k_2$, $C_1$, $C_2$ may be simultaneously estimated when temperatures are measured and the heat flux is prescribed. Equation (14) also indicates that the temperature rise is decreased by the $T_2-T_1$ sensitivity.

Figure 8:
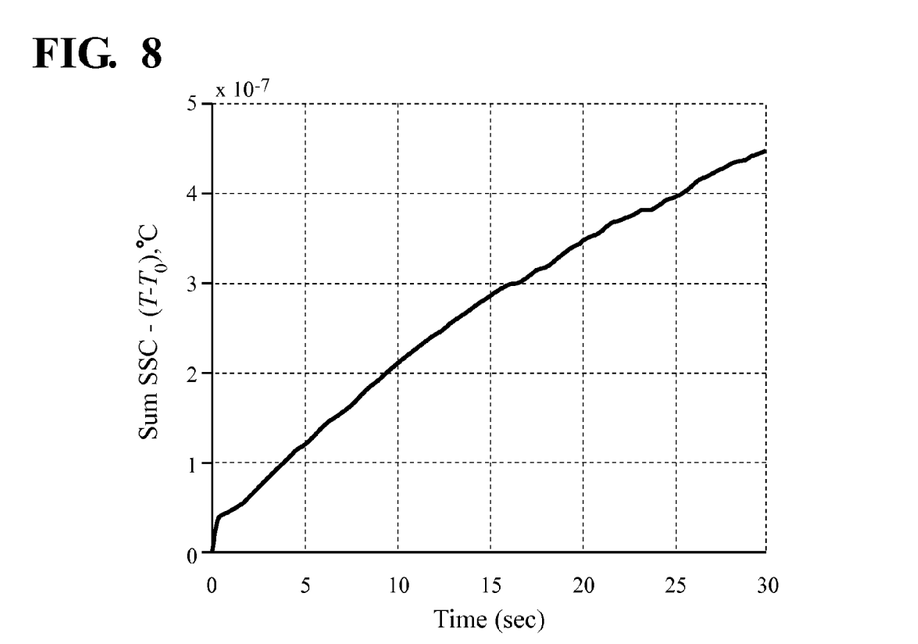
FIG. 8 is a graph showing a relationship between experimental time (s) and a summation of sensitivity coefficients.

The relationship between time (s) and the summation of the sensitivity coefficients from Equation (14) is shown in the graph depicted in FIG. 8. It is appreciated that the values are very close to zero, which suggests that the problem solved above passed the intrinsic verification test.

Figure 9:
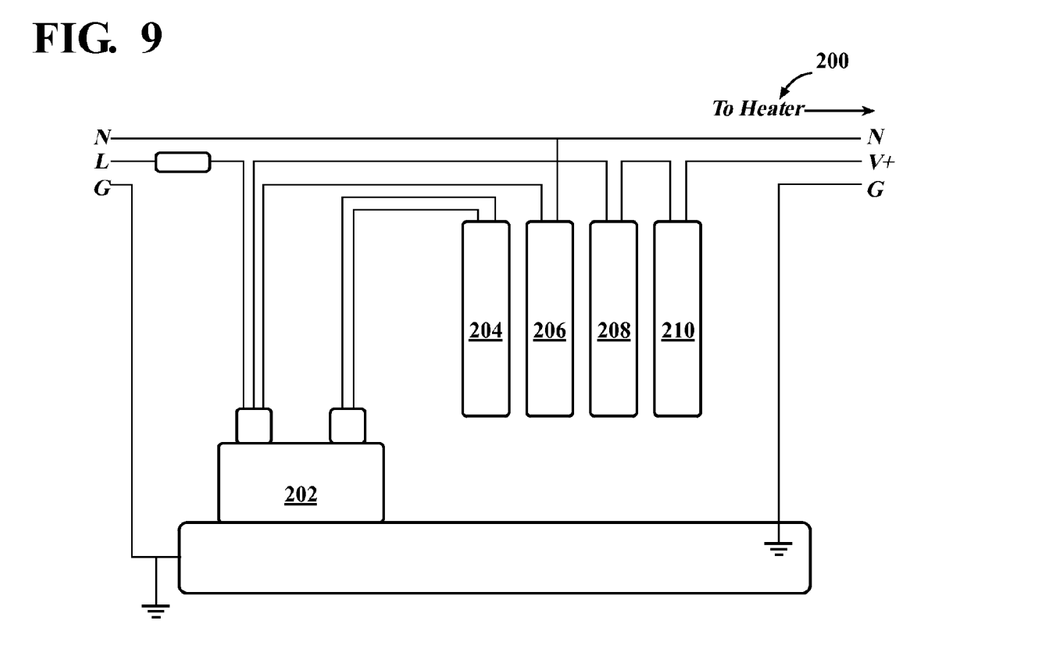
FIG. 9 schematically depicts an example of an instrumentation for the examples of the testing system.

Development of the instrumentation 200 for the testing system 10 and the pressurized housing 24 to operate at temperatures above 100° C. will now be described. A schematic of the instrumentation 200 is shown in FIG. 9. The instrumentation 200 is generally capable of generating different heating profiles, which requires a voltage output module. The voltage output module has adjustable settings, and includes a voltage control device 202 to send the voltage information to the heating element 62. It is believed that this instrumentation 200 will allow for better control of the heating rate of the material 40. Further, the program run by the controller 100 of the monitoring system 14 includes settings for the heating profile. The voltage control module generates the desired volts (using the volt setting 204), and the voltage 206 and ampere 208 loggers are in-line to record the power going through the heating element 62. A relay 210 may also be added as a safety feature. If, for example, the temperature rise is more than desired, then the relay 210 would turn off the system. The relay 210 can also act as a unit that can maintain a certain temperature in the container.

One of the advantages of the instrumentation shown in FIG. 9 is that it will allow simultaneous estimation of temperature-dependent thermal conductivity and specific heat. Further, the sum of scaled sensitivity coefficients of the parameters in Equation (14) is equal to the temperature rise, and all of the properties can be estimated individually.

Additionally, the heating profile of the instrumentation is an important factor for the estimation of the properties and/or parameters. Certain materials, such as food and other biological materials, are very sensitive to temperature change. An optimal heating profile may be needed for each category of materials. Further, a heating profile that is optimum for a high-conductive material might not be suitable for a low-conductive material. Optimum heating profiles are then generated for various categories of materials based on their thermal conductivity.

Additionally, a sequential method of estimation may be used to estimate the thermal properties of the material 40. Sequential estimation is a robust tool that may be used to check if the estimated properties are reliable. For instance, when the value of property does not come to a constant toward the end of an experiment, then there is some error in the model or in the experiment. It is believed that sequential parameter estimation can help to diagnose the error.

It is to be understood that the resistance of the heating element 62 can also be used as a temperature indicator. Accordingly, another method of estimating the thermal properties of a material utilizes resistance measurements which replaces the thermocouples used to measure the temperature of the material 40. It is believed that this method will provide a more accurate temperature measurement and estimation of the thermal properties with less error.

In this method, a transient heat conduction equation for a hollow housing 24 is given by Equation (15). This equation is used for estimating temperature-variable thermal conductivity and volumetric heat capacity (caused by changes in the specific heat) of the material 40 when the heating element 62 is located at the center of the housing 24.

$$\frac{1}{r}\frac{\partial}{\partial r}\left[k_h r \frac{\partial T}{\partial r}\right] + \frac{\partial}{\partial z}\left[k_h \frac{\partial T}{\partial z}\right] + g_0 f(t) = C_h \frac{\partial T}{\partial t} \quad \text{Equ. (15)}$$
for $R_0 < r < R_1, 0 < z < Z, t > 0$ $$\frac{1}{r}\frac{\partial}{\partial r}\left[k_1 f_k r \frac{\partial T}{\partial r}\right] + \frac{\partial}{\partial z}\left[k_1 f_k(T,K) \frac{\partial T}{\partial z}\right] = C_1 f_C \frac{\partial T}{\partial t}$$
for $R_1 < r < R_2, 0 < z < Z, t > 0$ Equation (15) may be solved numerically, such as by a finite element program or software. Numerical codes and verification of the numerical codes are also useful in this method. In this example, IVM is used in the numerical solution of the partial differential equation is presented below, along with a derivation of the dimensionless form of scaled sensitivity coefficients. The sum of scaled sensitivity coefficients is used in the dimensionless form to provide a method for verification.

In an example, Equation (16) represents a simple function:

$$T = f(k, C, x, t) \quad \text{Equ. (16)}$$

where k and C are parameters of the function T. The sensitivity coefficient of k and C are $$\frac{\partial T}{\partial k} \text{ and } \frac{\partial T}{\partial C},$$

respectively. After multiplying the sensitivity coefficient with the parameter, the scaled sensitivity coefficient represented by $$\hat{X}_k = k \frac{\partial T}{\partial k} \text{ and } \hat{X}_C = C \frac{\partial T}{\partial C}$$

for k and C, respectively, are obtained.

For the numerical code verification, the heat conduction problem is made dimensionless. Equation (17) shows the dimensionless parameters for k and C:

$$\tilde{k} = \frac{k_2}{k_1}, \tilde{C} = \frac{C_2}{C_1} \quad \text{Equ. (17)}$$

Linear functions of temperature for the thermal conductivity and volumetric heat capacity are considered, as shown by Equations (18) and (19):

$$f_k(T - T_0, \tilde{k}) = 1 + \frac{(T - T_0) - (T_1 - T_0)}{(T_2 - T_0) - (T_1 - T_0)}(\tilde{k} - 1) \quad \text{Equ. (18)}$$

$$f_C(T - T_0, \tilde{C}) = 1 + \frac{(T - T_0) - (T_1 - T_0)}{(T_2 - T_0) - (T_1 - T_0)}(\tilde{C} - 1) \quad \text{Equ. (19)}$$

which gives the thermal conductivity value of $k_1$ at $T_1$ and $k_2$ at $T_2$. The temperature dependence causes Equations (18) and (19) to be linear in T. The boundary conditions are shown by Equation (20):

$$\frac{\partial T}{\partial r}(R_3, z, t) = 0 \quad \frac{\partial T}{\partial z}(r, 0, t) = 0 \quad \frac{\partial T}{\partial z}(r, Z, t) = 0 \quad \text{Equ. (20)}$$

and the initial condition is shown by Equation (21):

$$T(r, z, 0) = T_0 \quad \text{Equ. (21)}$$

Also, Equation (22) is considered:

$$\tilde{k}_h \equiv \frac{k_h}{k_1}, \tilde{C}_h \equiv \frac{C_h}{C_1} \quad \text{Equ. (22)}$$

The above problem is put into a dimensionless form, as shown by Equations (23) and (24):

$$\tilde{r} \equiv \frac{r}{R_1}, \quad \text{Equ. (23)}$$

$$\tilde{R}_2 \equiv \frac{R_2}{R_1},$$

$$\tilde{z} \equiv \frac{z}{R_1},$$

$$\tilde{t} \equiv \frac{k_1 t}{C_1 R_1^2},$$

$$\tilde{k} \equiv \frac{k_2}{k_1},$$

$$\tilde{C} \equiv \frac{C_2}{C_1},$$

$$\tilde{k}_h \equiv \frac{k_h}{k_1},$$

$$\tilde{C}_h \equiv \frac{C_h}{C_1},$$

and $$\tilde{T} \equiv \frac{T - T_0}{\frac{g_0 R_1^2}{k_1}}, \tilde{T}_1 \equiv \frac{T_1 - T_0}{\frac{g_0 R_1^2}{k_1}}, \tilde{T}_2 \equiv \frac{T_2 - T_0}{\frac{g_0 R_1^2}{k_1}} \quad \text{Equ. (24)}$$

With the foregoing equations and with a known volumetric heat generation, the dimensionless temperature is given symbolically by Equation (25):

$$\tilde{T} = \tilde{T}(\tilde{r}, \tilde{R}_2, \tilde{z}, \tilde{t}, \tilde{k}, \tilde{C}, \tilde{k}_h, \tilde{C}_h, \tilde{T}_1, \tilde{T}_2) \quad \text{Equ. (25)}$$

Furthermore, the partial derivatives of temperature T are found, as shown by Equation (26):

$$T - T_0 = \frac{gR_1^2}{k_1}\tilde{T} \quad \text{Equ. (26)}$$

$$\begin{pmatrix} \tilde{r}, \tilde{R}_2, \tilde{z}, \tilde{t}(k_1, C_1)\tilde{k}(k_1, k_2), \tilde{C}(C_1, C_2), \dots \\ \tilde{k}_h(k_h, k_1), \tilde{C}_h(C_h, C_1), T_1(k_1, T_1 - T_0), T_2(k_1, T_2 - T_0) \end{pmatrix}$$

The scaled sensitivity coefficient with respect to $k_1$ is shown by Equation (27):

$$\hat{X}_{k_1} = \quad \text{Equ. (27)}$$

$$-\frac{g_0 R_1^2}{k_1}\tilde{T} + \frac{g_0 R_1^2}{k_1}\left[\tilde{t}\frac{\partial \tilde{T}}{\partial \tilde{t}} - \tilde{k}\frac{\partial \tilde{T}}{\partial \tilde{k}} - \tilde{k}_h\frac{\partial \tilde{T}}{\partial \tilde{k}_h} + T_1\frac{\partial \tilde{T}}{\partial \tilde{T}_1} + \tilde{T}_2\frac{\partial \tilde{T}}{\partial \tilde{T}_2}\right]$$

Additionally, the derivative is repeated with respect to $k_2$ and $k_h$ to obtain Equations (28) and (29):

$$\hat{X}_{k_2} = \frac{g_0 R_1^2}{k_1} \left[ \tilde{k} \frac{\partial \tilde{T}}{\partial \tilde{k}} \right] \quad \text{Equ. (28)}$$

$$\hat{X}_{k_h} = \frac{g_0 R_1^2}{k_1} \left[ \tilde{k}_h \frac{\partial \tilde{T}}{\partial \tilde{k}_h} \right] \quad \text{Equ. (29)}$$

The scaled sensitivity coefficients for $C_1$ and $C_2$ and $C_h$ are shown by Equations (30), (31), and (32):

$$\hat{X}_{C_1} = \frac{g_0 R_1^2}{k_1} \left[ -\tilde{t} \frac{\partial \tilde{T}}{\partial \tilde{t}} - \tilde{C} \frac{\partial \tilde{T}}{\partial \tilde{C}} - \tilde{C}_h \frac{\partial \tilde{T}}{\partial \tilde{C}_h} \right] \quad \text{Equ. (30)}$$

$$\hat{X}_{C_2} = \frac{g_0 R_1^2}{k_1} \left[ \tilde{C} \frac{\partial \tilde{T}}{\partial \tilde{C}} \right] \quad \text{Equ. (31)}$$

$$\hat{X}_{C_h} = \frac{g_0 R_1^2}{k_1} \left[ \tilde{C}_h \frac{\partial \tilde{T}}{\partial \tilde{C}_h} \right] \quad \text{Equ. (32)}$$

Next, the derivative with respect to $T_1-T_0$ and $T_2-T_0$ is found as shown in Equations (33) and (34):

$$\hat{X}_{(T_1-T_0)} = \frac{g_0 R_1^2}{k_1} \tilde{T}_1 \frac{\partial \tilde{T}}{\partial \tilde{T}_1} \quad \text{Equ. (33)}$$

$$\hat{X}_{(T_2-T_0)} = \frac{g_0 R_1^2}{k_1} \tilde{T}_2 \frac{\partial \tilde{T}}{\partial \tilde{T}_2} \quad \text{Equ. (34)}$$

Adding Equations (27) through (32) while subtracting Equations (33) and (34) give Equation (36):

$$\hat{X}_{k_1}+\hat{X}_{k_2}+\hat{X}_{k_h}+\hat{X}_{C_1}+\hat{X}_{C_2}+\hat{X}_{C_h}+\hat{X}_{(T_1-T_0)}+\hat{X}_{(T_2-T_0)}+(T-T_0) = 0 \quad \text{Equ. (35)}$$

The first six scaled sensitivity coefficients in Equation (35) are for fixed x and t values. The final two derivatives are the rate of change in the computed temperature when the specified temperature $T_1$ or $T_2$ is changed. Equation (35) indicates that the four parameters $k_1$, $k_2$, $C_1$, $C_2$ may be simultaneously estimated when temperatures are measured and the volumetric heat generation is prescribed. Equation (35) also indicates that the temperature rise is decreased by the $T_1-T_0$ and $T_2-T_0$ sensitivity.

In this example method, the design of the equipment is based on the mathematical model given by Equation (15). Using the inverse method, the thermal parameters can be estimated simultaneously within the desired temperature range, which are representative of current processing temperatures.

In an example, the method further includes a sequential method of estimation, which updates properties as new observations are inputted. Sequential estimation of properties in a model provides good insight into building the model and determining uncertainty in properties. For example, if properties come to a constant value after a certain reasonable time, then the experiment can be stopped as further data may not improve the property estimation. Prior information of properties can be used in sequential estimation towards estimation of properties for a particular experiment. The quality of the model for a given data set is judged by how well each property approaches a constant before the end of the experiment.

In an example, sequential estimation of thermal conductivity and volumetric specific heat may be accomplished using a matrix inversion method based on a Gauss minimization process. The mathematical form of non-linear sequential estimation is generally derived from a maximum a posteriori (MAP) estimation. The minimization function in the Gauss method can be expressed by Equation (36):

$$S=[Y-\hat{Y}(\beta)]^T W[Y-\hat{Y}(\beta)]+[\mu-\beta]^T U[\mu-\beta] \quad \text{Equ. (36)}$$

where Y is the experimental response variable, $\hat{Y}$ is predicted response, $\mu$ is prior information of parameter vector $\beta$, W is inverse of covariance matrix of errors, and U is the inverse of covariance matrix of the parameters. The extremum of the function given by Equation (36) can be evaluated by differentiating the equation with respect to $\beta$. The expression can be given as Equation (37):

$$\nabla_\beta S = -2[\nabla_\beta \hat{Y}(\beta)]^T W[Y-\hat{Y}(\beta)]-2[U][\mu-\beta] \quad \text{Equ. (37)}$$

In an example, Equation (37) can be set to zero, and $\nabla$ can be solved for implicitly. Standard statistical assumptions that allow the use of sequential estimation include additive errors, zero mean, uncorrelated errors, normally distributed errors, and covariance matrix of errors. No errors in independent variables and subjective prior information of properties are generally known. One way of estimating the properties is using an iterative scheme, as shown by Equations (38) through (43) below:

$$A_{i+1}=P_i X_{i+1}^T \quad \text{Equ. (38)}$$

$$\Delta_{i-1}=\phi_{i+1}+X_{i+1}A_{i+1} \quad \text{Equ. (39)}$$

$$K_{i+1}=A_{i+1}\Delta_{i+1}^{-1} \quad \text{Equ. (40)}$$

$$e_{i+1}=Y_{i+1}-\hat{Y}_{i+1} \quad \text{Equ. (41)}$$

$$b_{i+1}^*=b_i^*+K_{i+1}[e_{i+1}-X_{i+1}(b_i^*-b)] \quad \text{Equ. (42)}$$

$$P_{i+1}=P_i-K_{i+1}X_{i+1}P_i \quad \text{Equ. (43)}$$

where $b^*_{i+1}$ is the updated parameter (p×1, p is the number of parameters) vector at time step i+1; $b^*_i$ is the parameter vector at the previous time step i; b is the parameter vector at the previous iteration; P is the covariance vector matrix of parameters (p×p), X is the sensitivity coefficient matrix (n×p), and e is the error vector. The scheme is started by providing parameter estimates, computing X and the error vector e, and assuming a matrix P. In an example, P is set as a Diagonal matrix of $10^5$. Matrix P, X and e are functions of b, and not of b*. The stopping criteria for b can be given by Equation (44):

$$\frac{|b_j^{k+1} - b_j^k|}{|b_j^k|+\delta_1} < \delta \quad \text{Equ. (44)}$$

where, j is the index for the number of properties. The magnitude of $\delta$ could be $10^{-4}$. Another small number is $\delta_1$ which is about $10^{-8}$ to avoid a problem when $b_j^k$ tends to zero.

Figure 10:
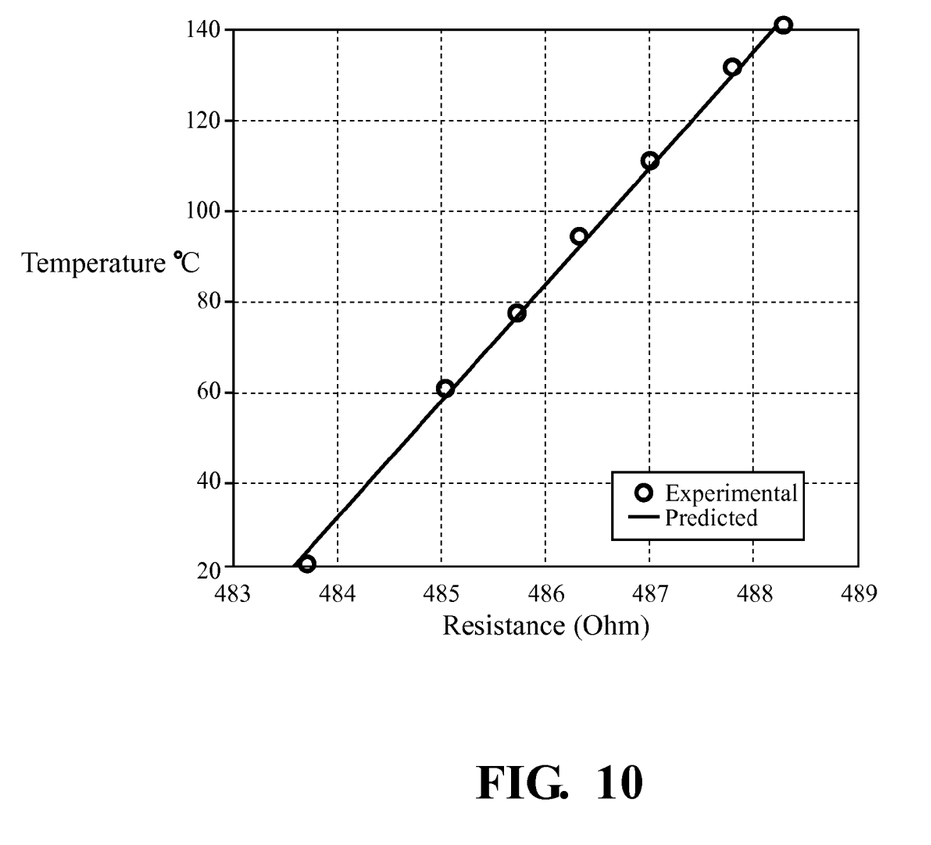
FIG. 10 is calibration curve for use in calibrating the resistance of a heating element of the testing system at a certain temperature.

It is to be understood that the heating element 62 is used as a temperature indicative device. The resistance of the heating element 62 is dependent on its temperature. This information may be used to calibrate the resistance of the heating element 62 at a certain temperature. Calibration may be performed, for example, using a silicon oil bath set at predetermined temperatures. A resistance meter may be used to measure the resistance of heating element 62 at a set temperature. An example of a calibration curve is presented in FIG. 10. The temperature (° C.) is plotted on Y-axis, and resistance (Ohm) is plotted on the X-axis. A linear relation was found between the resistance and temperature as given by Equation (45):

$$T = 26.118R - 12609 \qquad \text{Equ. (45)}$$

After verification of finite element program, data collected from the testing system 10 may be analyzed using the sequential estimation procedure described above.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

While the invention has been described in terms of various specific embodiments, those skilled in the art will recognize that the invention may be practiced with modification within the spirit and scope of the claims.

What is claimed is:

1. A testing system for use in measuring at least one thermal property of material, the testing system comprising:
    a testing apparatus comprising:
        a housing assembly having a sidewall comprising a first end, a second end, and an inner surface that defines a cavity extending between the first and second ends along a longitudinal axis, the housing assembly configured to receive a material;
        a fluid supply system coupled to the housing assembly and configured to supply a pressurized fluid into the cavity to pressurize the housing;
        a heating assembly coupled to the housing assembly and comprising at least one heating element positioned within the cavity, the at least one heating element extending along the longitudinal axis and at least partially through the material, the heating assembly configured to supply a heat to at least a portion of the material to increase a temperature of the material; and
        a sensing assembly coupled to the housing assembly comprising at least one sensing element positioned within the cavity and within the material, the at least one sensing assembly configured to sense a temperature of the material; and
    a monitoring system coupled to the testing apparatus and comprising a controller in communication with the heating assembly and the sensing assembly, the controller having a processor comprising computer-readable instructions for:
        operating the heating assembly to apply a heat to the material;
        receiving a signal from the sensing assembly, the signal being indicative of a temperature of the material; and
        estimating the at least one thermal property of the material from the sensed temperature of the material.

2. The testing system in accordance with claim 1, wherein the sensing assembly is configured to sense a temperature of the material at a plurality of locations within the material.

3. The testing system in accordance with claim 1, wherein the sensing assembly is configured to sense a temperature of the material at a plurality of sensing locations extending radially outwardly from the at least one heating element, each sensing location being spaced radially outwardly from an adjacent sensing location.

4. The testing system in accordance with claim 1, wherein the sensing assembly is configured to sense a temperature of the material at a plurality of locations within the material along the longitudinal axis.

5. The testing system in accordance with claim 1, wherein the processor of the controller further comprises computer-readable instructions for:
    controlling the heating assembly to increase the heat applied to the material over a predefined period of time;
    obtaining data from the sensing system that represents a temperature increase within the material over the predefined period of time;
    calculating a rate of change in the temperature of the material within the predefined period of time; and
    estimating at least one thermal property of the material from the calculated temperature change.

6. A testing apparatus of a testing system for estimating a thermal property of a material, the testing apparatus comprising:
    a housing assembly comprising a first end, a second end, and an inner surface that defines a cavity extending between the first second ends along a longitudinal axis, the housing assembly configured to receive a material;
    a fluid supply system coupled to the housing and configured to selectively supply a pressurized fluid into the cavity to pressurize the housing;
    a heating assembly coupled to the housing assembly and comprising at least one heating element positioned within the cavity and extending along the longitudinal axis and at least partially within the material, the heating assembly configured to apply a heat to at least a portion of the material to increase a temperature of the material;
    a sensing assembly coupled to the housing assembly and comprising at least one sensing element positioned within the cavity, the at least one sensing element positioned within the material and configured to sense a temperature of the material; and
    a processor comprising computer-readable instructions for estimating the thermal property of the material utilizing the sensed temperature of the material.

7. The testing apparatus in accordance with claim 6, wherein the heating assembly further comprises:
    a power supply assembly coupled to the at least one heating element for providing power to the heating element, the power supply assembly configured to selectively adjust a power voltage supplied to the heating element to adjust the heat supplied to the material; and
    a temperature controller coupled to the power supply assembly and to the sensing assembly, the temperature controller configured to sense a temperature of at least one of the material and the housing assembly and to operate the power supply assembly to adjust the heat supplied to the material from at least one of the sensed material temperature and the sensed housing assembly temperature.

8. The testing apparatus in accordance with claim 6, wherein the sensing assembly includes a plurality of sensing elements, and wherein adjacent sensing elements are spaced radially outwardly from the at least one heating element for sensing a temperature of the material at a plurality of radial locations within the material.

9. The testing apparatus in accordance with claim 8, wherein each sensing element is orientated within the same plane.

10. The testing apparatus in accordance with claim 6, wherein the sensing assembly includes a plurality of axially-spaced sensing elements, and wherein each sensing element is orientated along the longitudinal axis for sensing a temperature of the material at a plurality of sensing locations spaced along the longitudinal axis.

11. The testing apparatus in accordance with claim 6, wherein the housing comprises a sidewall, and wherein the sensing assembly includes at least on sensing element orientated with respect to the housing sidewall for sensing a temperature of the housing sidewall.

12. A method of estimating at least one thermal property of a material in a testing apparatus comprising a housing assembly configured to house the material, a heating assembly coupled to the housing assembly, and a sensing assembly coupled to the housing assembly, the method comprising the steps of:
    applying a heat to a material with the heating assembly at a heating location to increase a temperature of the material;
    sensing a temperature of the material with the sensing assembly at a plurality of sensing locations each spaced radially outwardly from the heating location and within the material and the housing assembly; and
    estimating at least one thermal property of the material from the sensed temperature at each sensing location.

13. The method in accordance with claim 12, further comprising the steps of:
    increasing the heat applied to the material with the heating assembly over a first period of time;
    sensing a temperature of the material at each sensing location with the sensing assembly over the first period of time;
    calculating a rate of change in temperature at each sensing location during the first period of time; and
    estimating the at least one thermal property from the calculated rate of temperature change at each sensing location during the first period of time.

14. The method in accordance with claim 13, further comprising the steps of:
    reducing the heat applied to the material upon sensing the temperature is approximately equal to a predefined temperature;
    sensing a temperature of the material at each sensing location with the sensing assembly over a second predefined period of time;
    calculating a rate of change in temperature at each sensing location during the second period of time; and
    estimating the at least one material thermal property from the calculated rate of temperature change at each sensing location during the second period of time.

15. The method in accordance with claim 12, further comprising the steps of:
    providing a fluid supply system coupled to the housing assembly; and
    supplying, with the fluid supply system, a fluid into the housing assembly to pressurize the housing assembly.

16. The method in accordance with claim 12, wherein the heating assembly extends along a longitudinal axis of the housing assembly and is at least partially within the material.

* * * * *